United States Patent
Cohen (10) Patent No.: US 7,361,163 B2
(45) Date of Patent: Apr. 22, 2008

(54) FLUID TRANSFER DEVICE HAVING REMOVABLE NEEDLE CARTRIDGE

(75) Inventor: Nahum Cohen, Karme Yosef (IL)

(73) Assignee: ADST Technologies. Ltd., Karme Yosef (IL)

( * ) Notice: Subject to any disclaimer, the term of this patent is extended or adjusted under 35 U.S.C. 154(b) by 84 days.

(21) Appl. No.: 10/868,764

(22) Filed: Jun. 17, 2004

(65) Prior Publication Data

US 2004/0260270 A1 Dec. 23, 2004

Related U.S. Application Data

(60) Provisional application No. 60/478,845, filed on Jun. 17, 2003.

(51) Int. Cl.
*A61M 5/00* (2006.01)
*B65D 83/10* (2006.01)

(52) U.S. Cl. .................. 604/232; 604/173; 206/366

(58) Field of Classification Search ........... 604/110, 604/173, 187, 195, 232, 506; 206/366; 600/309; 606/181–182

See application file for complete search history.

(56) References Cited

U.S. PATENT DOCUMENTS

| 4,518,384 | A | * | 5/1985 | Tarello et al. ............... 604/61 |
| 5,285,896 | A | * | 2/1994 | Salatka et al. ............. 206/366 |
| 5,318,522 | A | | 6/1994 | D'Antonio |
| 5,829,589 | A | * | 11/1998 | Nguyen et al. ............. 206/366 |
| 6,032,543 | A | | 3/2000 | Arthum et al. |
| 6,056,716 | A | * | 5/2000 | D'Antonio et al. ........... 604/68 |
| 6,610,042 | B2 | * | 8/2003 | Leon et al. ................. 604/500 |
| 6,783,537 | B1 | * | 8/2004 | Kuhr et al. ................. 606/182 |
| 2003/0083686 | A1 | * | 5/2003 | Freeman et al. ........... 606/181 |
| 2003/0173048 | A1 | * | 9/2003 | Buchanan et al. .......... 162/352 |

* cited by examiner

*Primary Examiner*—Kevin C. Sirmons
*Assistant Examiner*—Andrew Gilbert
(74) *Attorney, Agent, or Firm*—AlphaPatent Associates Ltd.; Daniel J. Swirsky (57) ABSTRACT

A fluid transfer device including a cartridge having a plurality of needles, an advancer operative to selectably advance any of the plurality of needles in the cartridge to a needle deployment position, and a syringe operative to convey fluid through the needle in the needle deployment position.

17 Claims, 12 Drawing Sheets

FLUID TRANSFER DEVICE HAVING REMOVABLE NEEDLE CARTRIDGE

CROSS-REFERENCE TO RELATED APPLICATIONS

This application claims the benefit of U.S. Provisional Patent Application Ser. No. 60/478,845, filed Jun. 17, 2003, entitled "Multi Needle Disposal Cartridge in Syringe Applications," and incorporated herein by reference in its entirety.

FIELD OF THE INVENTION

The present invention relates to a fluid transfer device having a removable cartridge containing multiple needles.

BACKGROUND OF THE INVENTION

When injections are administered to a large number of animals, the same needle is often repeatedly used. This is due primarily to the need to carry out mass injections quickly and efficiently, whereas employing multiple needles is time-consuming, cumbersome, and potentially unsafe due to the burden their disposal places upon those giving the injections. However, reusing the same needle is unsanitary and may lead to the spread of disease from one animal to the next. An efficient solution that allows multiple injections to be performed quickly and efficiently, provides a separate, sterile needle for each subject, and provides for safe, easy needle disposal would therefore be advantageous.

SUMMARY OF THE INVENTION

The present invention discloses a fluid transfer device employing a removable cartridge having multiple needles, where the cartridge is automatically advanced to the next unused needle after a needle has been used, until all of the needles in the cartridge have been used once. The cartridge provides a protective housing for both unused and used needles.

The present invention may be used in veterinary medicine, where a group of animals may require injections at one time, although it is appreciated that it may be used in other applications as well. Using the device of the present invention, a separate, sterile needle is employed for each injection, reducing the risk of disease transfer from one subject to the next. The required amount of fluid to be administered may be set only once for a series of injections. Thus, a uniform dosage may be administered to a large number of subjects with relative ease.

In one aspect of the present invention a fluid transfer device is provided including a cartridge including a plurality of needles, an advancer operative to selectably advance any of the plurality of needles in the cartridge to a needle deployment position, and a syringe operative to convey fluid through the needle in the needle deployment position.

In another aspect of the present invention the device further includes apparatus operative to at least partially extend the needle out of the cartridge.

In another aspect of the present invention the apparatus is retractable to urge the needle at least partially back into the cartridge.

In another aspect of the present invention the device further includes an syringe operative to couple with the needle for conveying the fluid therethrough.

In another aspect of the present invention the cartridge includes a plurality of needle chambers, each chamber housing one of the plurality of needles.

In another aspect of the present invention any of the chambers includes a spring operative to expand when the needle is extended at least partially out of the chamber and contract to retract the needle at least partially back into the chamber.

In another aspect of the present invention any of the chambers includes at least one needle guard operative to at least partially obstruct an opening of the chamber subsequent to the needle being firstly extended at least partially out of the chamber, where the obstruction is sufficient to prevent reentry into the chamber of apparatus for extending the needle out of the chamber.

In another aspect of the present invention the needle guard is flexed and held in place between the needle and an inner wall of the chamber prior to the needle being firstly extended at least partially out of the chamber, and where the needle guard resiliently flattens at least partially across the opening of the chamber subsequent to the extending of the needle.

In another aspect of the present invention the cartridge is cylindrical and is operative to be rotated to advance any of the needles to the needle deployment position.

In another aspect of the present invention the cartridge is a ribbon in which a plurality of needle chambers are disposed.

In another aspect of the present invention the cartridge is a sliding cartridge and is operative to be slid along an axis to advance any of the needles to the needle deployment position.

In another aspect of the present invention a method is provided for fluid transfer, the method including selectably advancing any of the plurality of needles in a cartridge to a needle deployment position, and conveying fluid through the needle in the needle deployment position.

In another aspect of the present invention the method further includes at least partially extending the needle out of the cartridge.

In another aspect of the present invention the method further includes at least partially retracting the needle back into the cartridge.

In another aspect of the present invention the method further includes coupling an syringe with the needle and conveying the fluid therethrough.

In another aspect of the present invention the method further includes housing each of the plurality of needles in a corresponding one of a plurality of needle chambers disposed in the cartridge.

In another aspect of the present invention the method further includes causing a spring disposed in any of the chambers to expand when the needle is extended at least partially out of the chamber and contract to retract the needle at least partially back into the chamber.

In another aspect of the present invention the method further includes at least partially obstructing an opening of any of the chambers subsequent to the needle being firstly extended at least partially out of the chamber, where the obstruction is sufficient to prevent reentry into the chamber of apparatus for extending the needle out of the chamber.

In another aspect of the present invention the method further includes flexing and holding a needle guard in place between the needle and an inner wall of the chamber prior to the needle being firstly extended at least partially out of the chamber, and flattening the needle guard at least partially across the opening of the chamber subsequent to the extending of the needle.

In another aspect of the present invention the method further includes rotating the cartridge to advance any of the needles to the needle deployment position, where the cartridge is cylindrical.

In another aspect of the present invention the method further includes sliding the cartridge along an axis to advance any of the needles to the needle deployment position, where the cartridge is a sliding cartridge.

BRIEF DESCRIPTION OF THE DRAWINGS

The present invention will be understood and appreciated more fully by way of example provided by the following detailed description taken in conjunction with the appended drawings in which.

DETAILED DESCRIPTION OF PREFERRED EMBODIMENTS

Figure 1A:
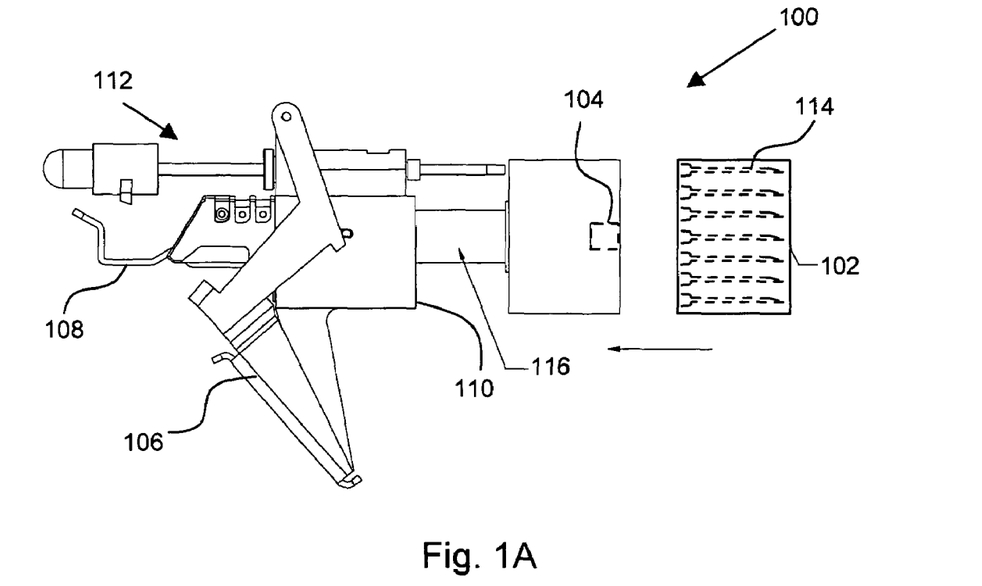
FIGS. 1A and 1B are simplified side views of a fluid transfer device, constructed and operative in accordance with a preferred embodiment of the present invention.
Figure 1B:
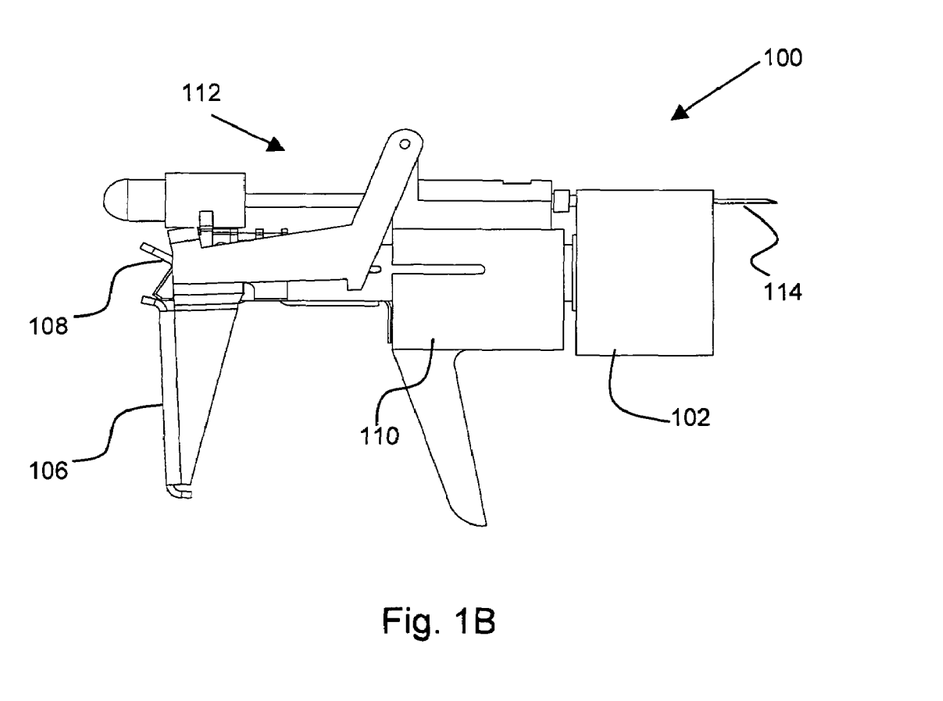

Reference is now made to FIGS. 1A and 1B, which are simplified side views of a fluid transfer device 100, constructed and operative in accordance with a preferred embodiment of the present invention. A fluid transfer device, generally designated 100, is shown to which a needle cartridge 102 is coupled. Cartridge 102 preferably houses multiple needles 114 and is adapted for being mounted to and dismounted from fluid transfer device 100, such as onto a shaft assembly 116, for which a locking mechanism 104, which may be any conventional locking mechanism, is provided on either shaft 116 or cartridge 102 so that cartridge 102 may be securely fastened to shaft assembly 116. Fluid transfer device 100 also preferably includes a handle 106, a safety latch 108, a main housing 110, and a piston assembly, generally designated 112, which operate in combination to advance cartridge 102 to the next needle 114 and convey a predetermined amount of fluid via a single needle 114.

Figure 2A:
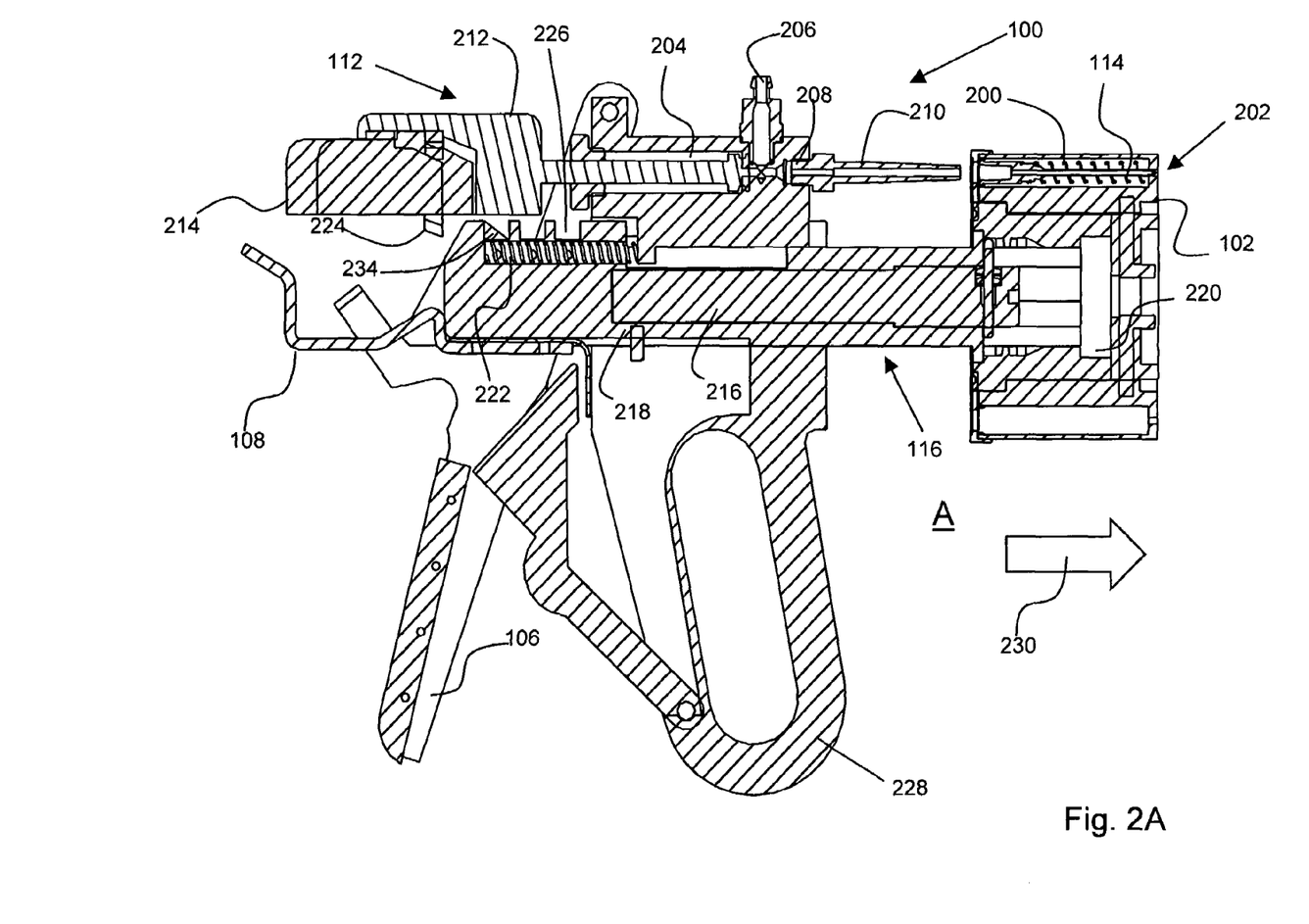
FIGS. 2A and 2B are simplified cross-sectional side views of a fluid transfer device, constructed and operative in accordance with a preferred embodiment of the present invention.
Figure 2B:
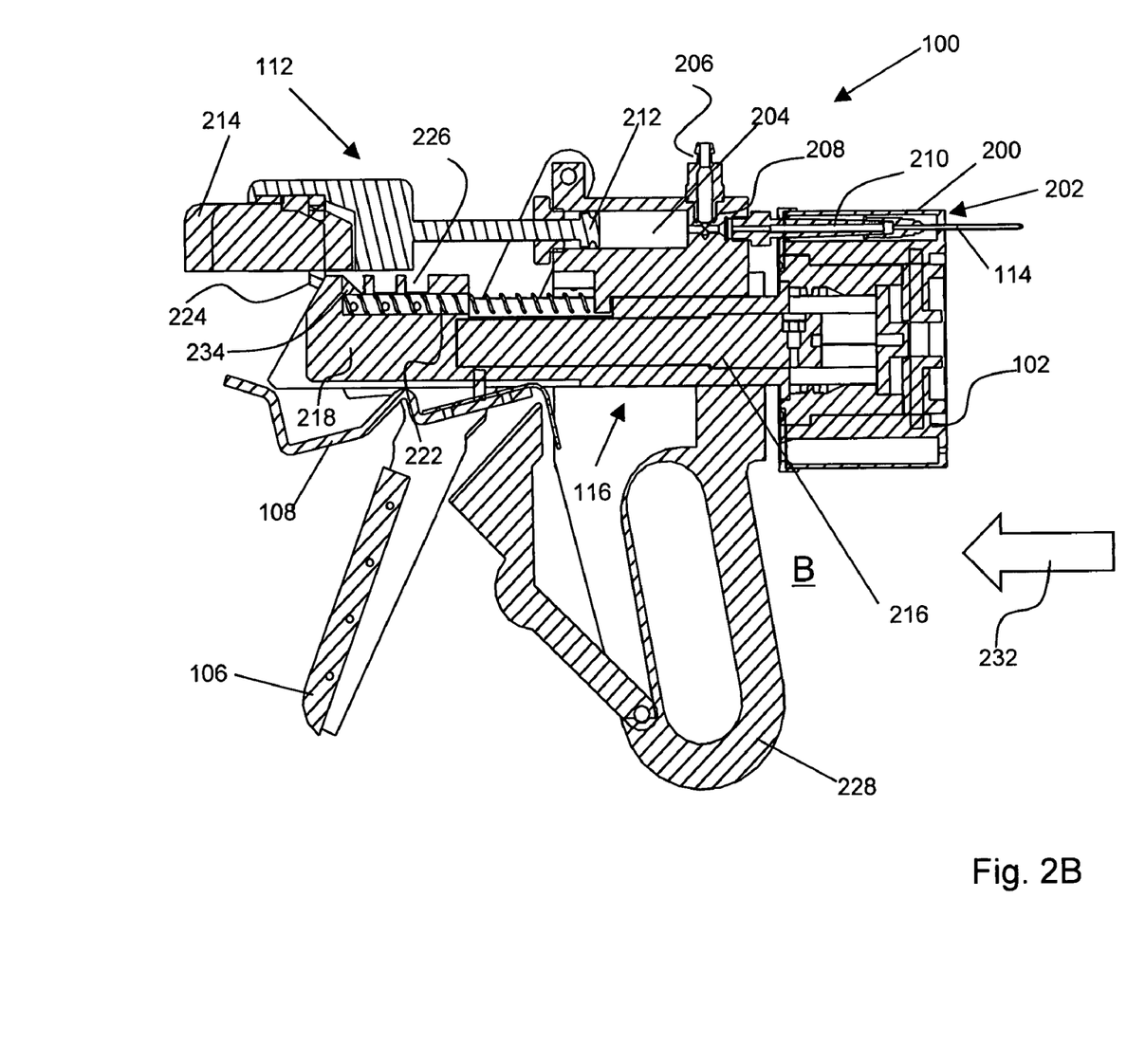

Reference is now made to FIGS. 2A and 2B, which represent simplified cross-sectional side views of fluid transfer device 100, constructed and operative in accordance with a preferred embodiment of the present invention. In FIGS. 2A and 2B, needle cartridge 102 is illustrated housing a plurality of needles 114, only one of which is shown for illustration purposes, in a predetermined arrangement. Cartridge 102 is preferably cylindrical and includes multiple needle chambers 200 for housing single needles 114 in a sterile and safe manner. In one possible configuration, twenty-four needle chambers housing twenty-four needles are positioned around the circumference of cartridge 102. It is appreciated, however, that cartridge 102 may be designed to house any suitable number of needles. Preferably, the upper-most needle in cartridge 102 occupies a needle deployment position 202. During operation of fluid transfer device 100, the needle 114 occupying needle deployment position 202 is forced outwardly from cartridge 102, enabling needle 114 to be inserted into a single subject, such as for the injection of fluid. Following injection, needle 114 is drawn back into its chamber 200 in cartridge 102, and cartridge 102 is rotated by a pre-set amount using any conventional means to allow an unused needle to occupy needle deployment position 202, such as is described in greater detail hereinbelow with reference to FIG. 9.

Piston assembly 112 preferably includes a fluid reservoir 204, and a first one-way valve 206 for facilitating entry of fluid into reservoir 204, such as via a tube or container connected to valve 206. Piston assembly 112 also preferably includes a second one-way valve 208 and a syringe 210. Second one-way valve 208 serves to enable passage of fluid from reservoir 204 to syringe 210. Piston assembly 112 also preferably includes a spring-biased piston 212 slidably mounted in reservoir 204, and a piston pusher 214 coupled to piston 212 and adapted to be pressed during operation of fluid transfer device 100 to urge fluid to flow from reservoir 204 to syringe 210. During an injection, syringe 210 temporarily couples with and pushes needle 114 outward from needle deployment position 202 such that needle 114 protrudes from cartridge 102 for insertion into a subject. This will be further described below.

Main housing 110 (FIG. 1A) is preferably connected to cartridge 102 via shaft assembly 116, and is movable, together with cartridge 102, between a priming position A, as shown in FIG. 2A, and an injecting position B, as shown in FIG. 2B. Shaft assembly 116 preferably includes an inner shaft 216, an outer shaft 218, and an advancer 220 coupled to cartridge 102 for advancing the next needle chamber 200 in cartridge 102 to needle deployment position 202, such as by rotating cartridge 102 by a predetermined amount, whenever main housing 110 is moved from injecting position B to priming position A. Main housing 110 also includes a main housing spring 222 positioned between outer shaft 218 and piston 212. In priming position A, main housing 110 and cartridge 102 are in an extended position with respect to piston assembly 112, and spring 222 is compressed. In injecting position B, main housing 110 and cartridge 102 are in a retracted position with respect to piston assembly 112.

In injecting position B, syringe 210 has entered cartridge 102 and has coupled with needle 114 in needle deployment position 202. Handle 106 and safety latch 108 preferably function to enable movement of main housing 110 and cartridge 102 between priming position A and injecting position B.

A piston jack 224 coupled to piston 212 is preferably adapted to recede upward into piston assembly 112 when piston 212 is pushed forward in the direction of arrow 230, and to extend downward out of piston assembly 112 when forward movement of piston 212 has ceased. A piston puller 234 is preferably disposed in one of several grooves 226 on outer shaft 218 of main housing 110, with each groove 226 corresponding to a predetermined dosage. After injection, outer shaft 218 preferably moves forward in the direction of arrow 230, where piston puller 234 is preferably sloped downward to allow it to engage and pass underneath a correspondingly sloped tip of piston jack 224. Outer shaft 218 then preferably moves backward in the direction of arrow 232, with piston puller 234 catching piston jack 224 and drawing piston 212 back. It will be seen that positioning piston puller 234 closer to reservoir 204 will cause piston puller 234 to engage piston jack 224 sooner, and cause more fluid to enter reservoir 204, while positioning piston puller 234 farther back from reservoir 204 will cause piston puller 234 to engage piston jack 224 later, and cause less fluid to enter reservoir 204. In this manner, the position of piston puller 234 may be set at the desired groove 226 to determine to the amount of fluid for each an injection.

Typical operation of fluid transfer device 100 begins by moving piston pusher 214 of piston assembly 112 back and forth so as to produce low pressure in reservoir 204. This motion is continued until fluid becomes drawn through tubing connecting fluid transfer device 100 to a fluid container (not shown) and into fluid transfer device 100 via first one-way valve 206. A desired fluid dosage that is to be administered to each subject is controlled by setting piston jack 224 into the desired groove 226 as described above. Needle cartridge 102 may then be attached to main housing 110.

Injection of a subject is carried out in three steps. First, handle 106 is pushed towards a grip 228. This results in the forward movement of main housing 110, outer shaft 218, inner shaft 216, and cartridge 102 in the direction of arrow 230 to priming position A, as seen in FIG. 2A. The forward movement of main housing 110 compresses main housing spring 222 and locks safety latch 108 onto outer shaft 218 of main housing 110. Pushing handle 106 also results in advancer 220 advancing cartridge 102 by a predetermined amount so as to present the next needle 114 to needle deployment position 202. Advancer 220 may function through any appropriate means in the art for converting the linear motion of main housing 110 into an advancing action of cartridge 102, such as through rotation. Next, safety latch 108 is pressed downward and released from outer shaft 218, resulting in backward movement of main housing 110 and cartridge 102 in the direction of arrow 232, as seen in FIG. 2B. The backward movement of cartridge 102 causes syringe 210 to enter cartridge 102, couple with needle 114 in needle deployment position 202, and to partially push needle 114 out of cartridge 102, whereupon needle 114 may then be inserted into a subject. The release of safety latch 108 also preferably causes spring 222 to expand, resulting in the backward movement of outer shaft 218 and piston 212, which causes a predetermined amount of fluid to be drawn into reservoir 204 via first one-way valve 206. In the third step, piston pusher 214 is pressed forward, resulting in passage of the predetermined amount of fluid from reservoir 204 to syringe 210 and into needle 114 for injection into the subject. It is appreciated that in this step, second one-way valve 208 is opened, and first one-way valve 206 is closed, so as to result in the movement of fluid as described. The above process is then repeated for subsequent subjects, with an unused needle being used for each injection.

Figure 3A:
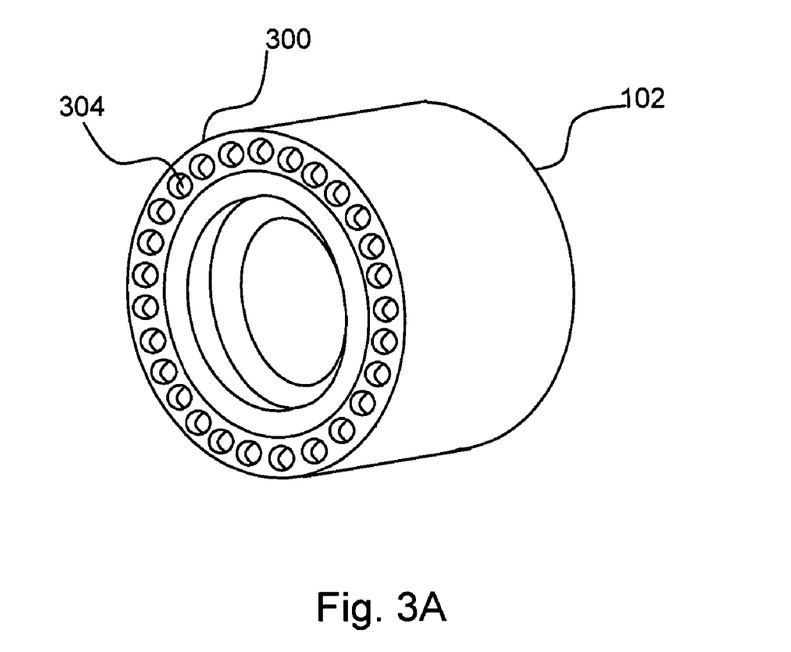
FIG. 3A is an isometric view, taken from the syringe entry side of the cartridge of the device illustrated in FIGS. 1 and 2.
Figure 3B:
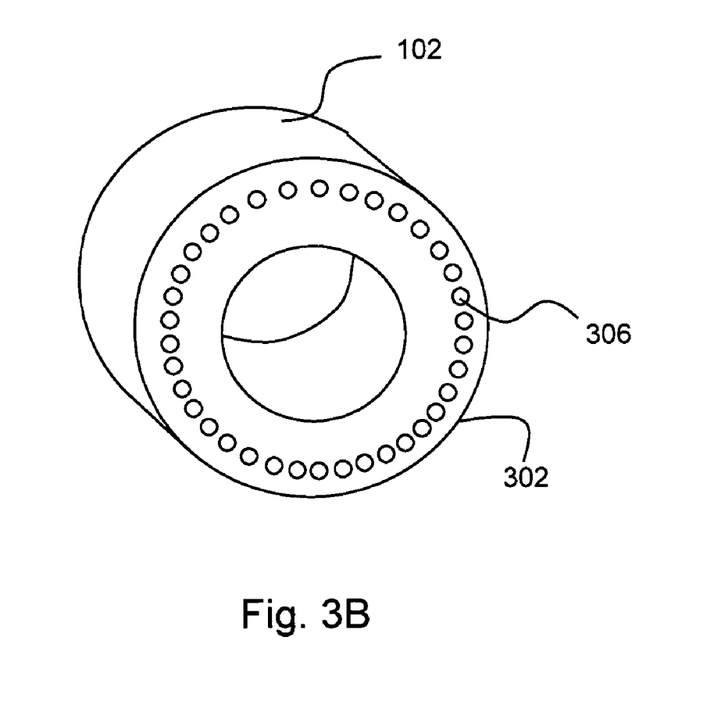
FIG. 3B is an isometric view, taken from the needle outlet side of the cartridge of the device illustrated in FIGS. 1 and 2.

Reference is now made to FIGS. 3A and 3B, which represent alternate isometric views, taken from a syringe entry side 300 and from an needle outlet side 302, respectively, of cartridge 102 shown in FIGS. 1 and 2. Syringe entry side 300 of cartridge 102 is shown having multiple openings 304, for enabling each needle to be engaged by syringe 210 (FIG. 2A) at the appropriate time during operation of the device. Needle outlet side 302 of cartridge 102 is shown having multiple corresponding needle outlet holes 306 for allowing outward movement of a single needle from cartridge 102 at the time of needle deployment.

Figure 4A:
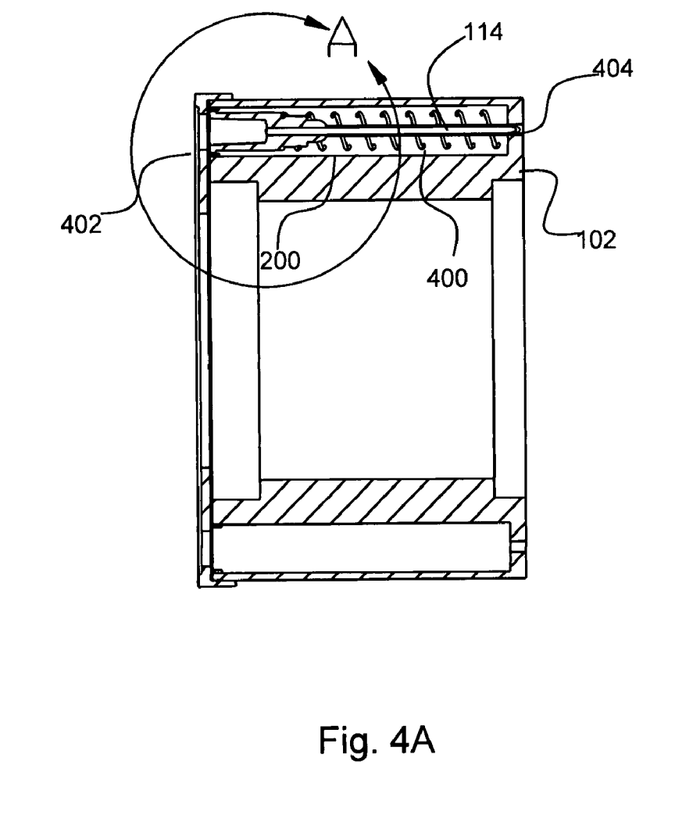
FIGS. 4A and 4B are partial cross-sectional side views of the cartridge of the device illustrated in FIGS. 1 and 2, showing a single needle chamber of the cartridge before needle deployment.
Figure 4B:
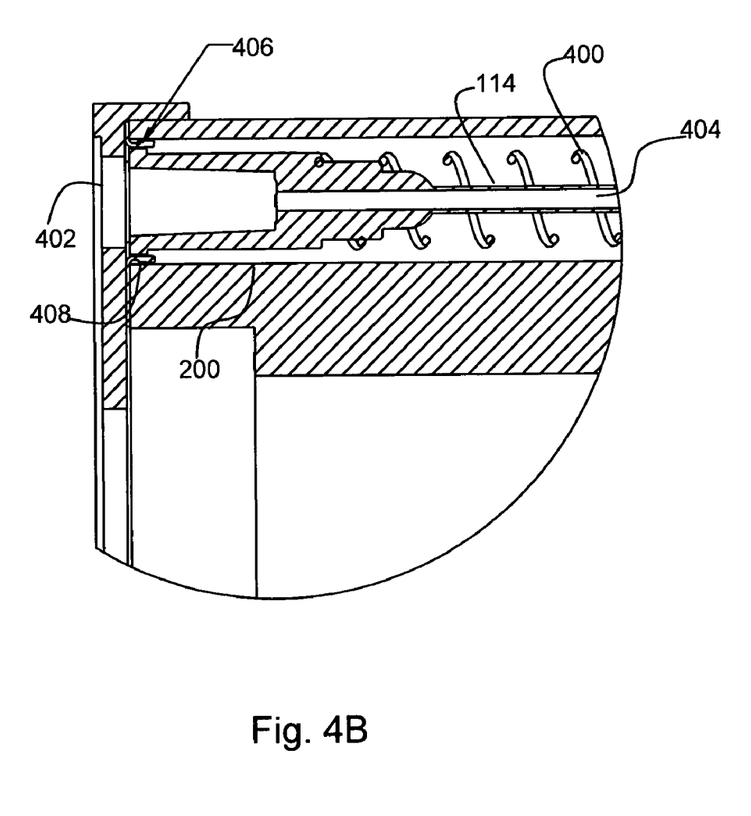
Figure 4C:
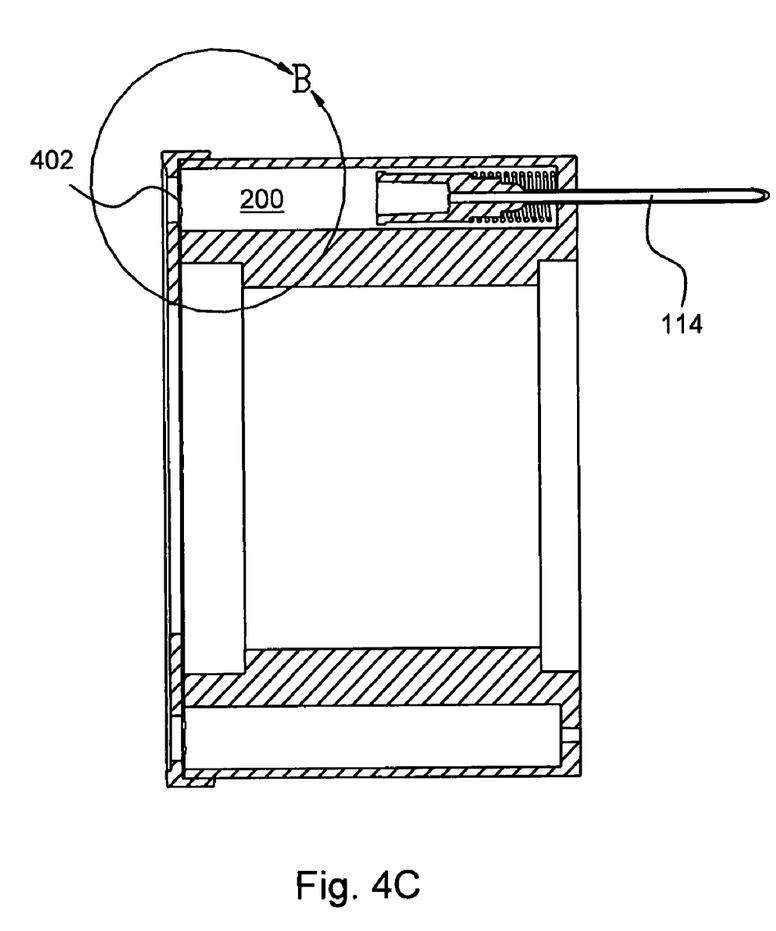
FIGS. 4C and 4D are partial cross-sectional side views of the cartridge of the device illustrated in FIGS. 1 and 2, showing a single needle chamber of the cartridge during needle deployment.
Figure 4D:
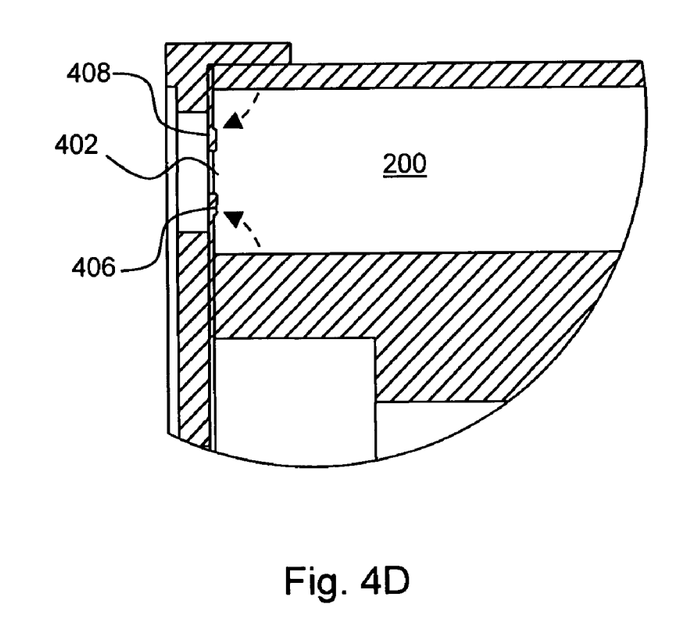
Figure 4E:
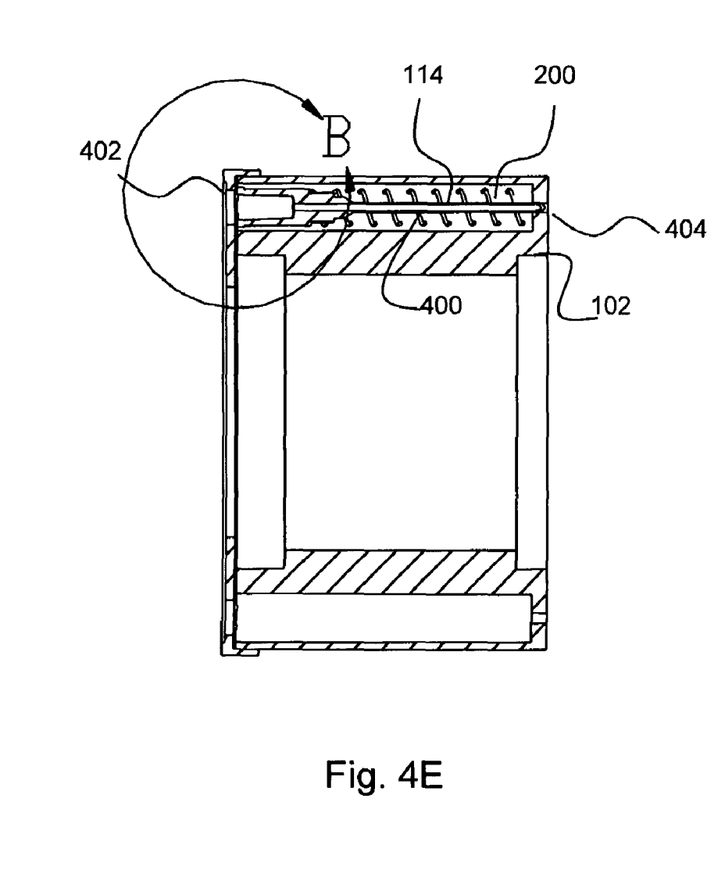
FIGS. 4E and 4F are partial cross-sectional side views of the cartridge of the device illustrated in FIGS. 1 and 2, showing a single needle chamber of the cartridge after the needle has returned to the cartridge.
Figure 4F:
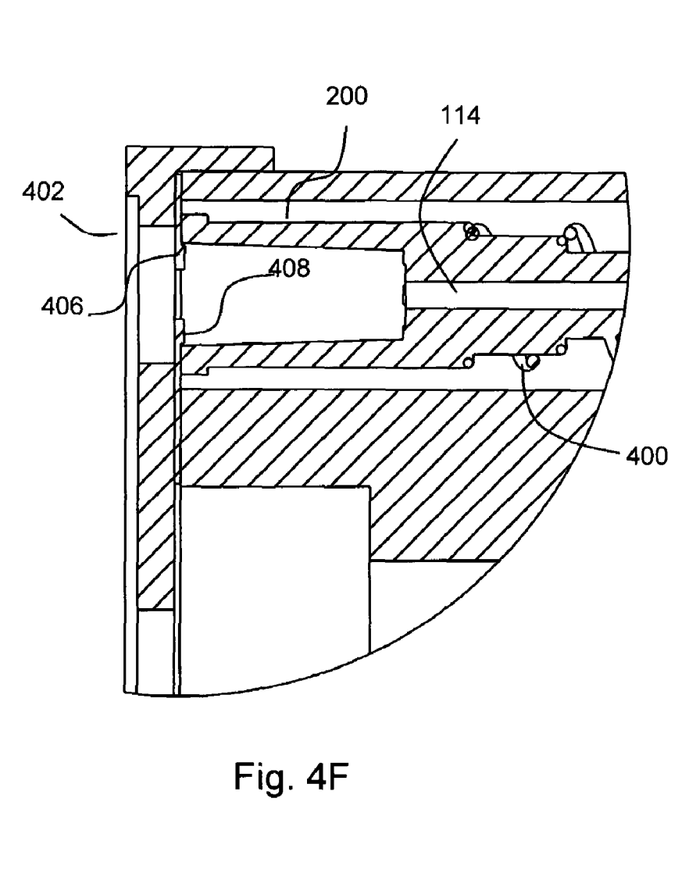

Reference is now made to FIGS. 4A and 4B, which are partial cross-sectional side views of the cartridge of the device illustrated in FIGS. 1 and 2, showing a single needle chamber of the cartridge before needle deployment, to FIGS. 4C and 4D, which are partial cross-sectional side views of the cartridge of the device illustrated in FIGS. 1 and 2, showing a single needle chamber of the cartridge during needle deployment, and to FIGS. 4E and 4F, which are partial cross-sectional side views of the cartridge of the device illustrated in FIGS. 1 and 2, showing a single needle chamber of the cartridge after the needle has returned to the cartridge. Each needle chamber 200 (FIG. 2A) preferably includes a needle spring 400 engaged around needle 114 for facilitating the return of needle 114 back into chamber 200 after use. Spring 400 preferably compresses against an outlet wall 404 of needle chamber 200 when syringe 210 pushes needle 114 out of needle chamber 200. When syringe 210 is withdrawn, the compression force abates, allowing spring 400 to urge needle 114 back into chamber 200.

A first needle guard 406, and preferably a second needle guard 408, are disposed at an entrance 402 of needle chamber 200 through which syringe 210 enters. Needle guards 406, 408 function to prevent reuse of a needle. Prior to the first use of needle 114, needle guards 406, 408 are flexed and held in place between the base of needle 114 and the inner walls of needle chamber 200, as shown in FIGS. 4A and 4B. When needle 114 is extended from cartridge 102, needle guards 406, 408 resiliently flatten, as shown in FIGS. 4C and 4D. This prevents further usage of needle 114, as the opening into needle chamber 200 in the fluid entry side of cartridge 102 which leads to needle 114 becomes effectively blocked, preventing the entry of syringe 210 into needle chamber 200.

Figure 5:
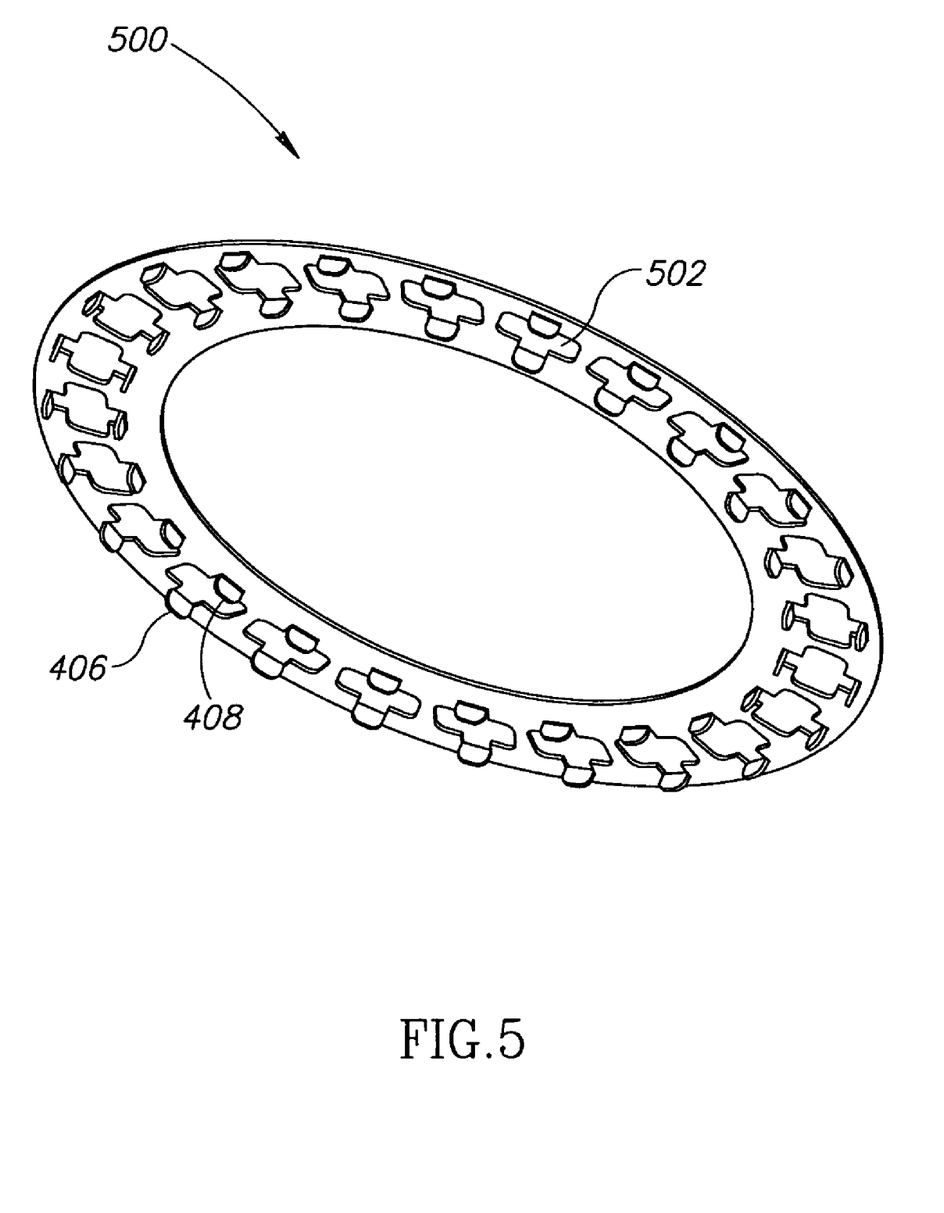
FIG. 5 is an isometric, bottom view of a needle guard ring for use with the cartridge of the device of FIGS. 1 and 2.

Reference is now made to FIG. 5, which is an isometric, bottom view of a needle guard ring for use with the cartridge of the device of FIGS. 1 and 2. A needle guard ring 500 is shown having a series of ring openings 502 on which first and second needle guards 406, 408 are disposed. Ring 500 is preferably positioned on the fluid entry side of cartridge 102 and provides each needle chamber 200 with first and second needle guards 406, 408. Ring 500 may be formed from flexible plastic or any other suitable material. In FIG. 5, needle guards 406, 408 are shown in a flexed configuration.

Figure 6:
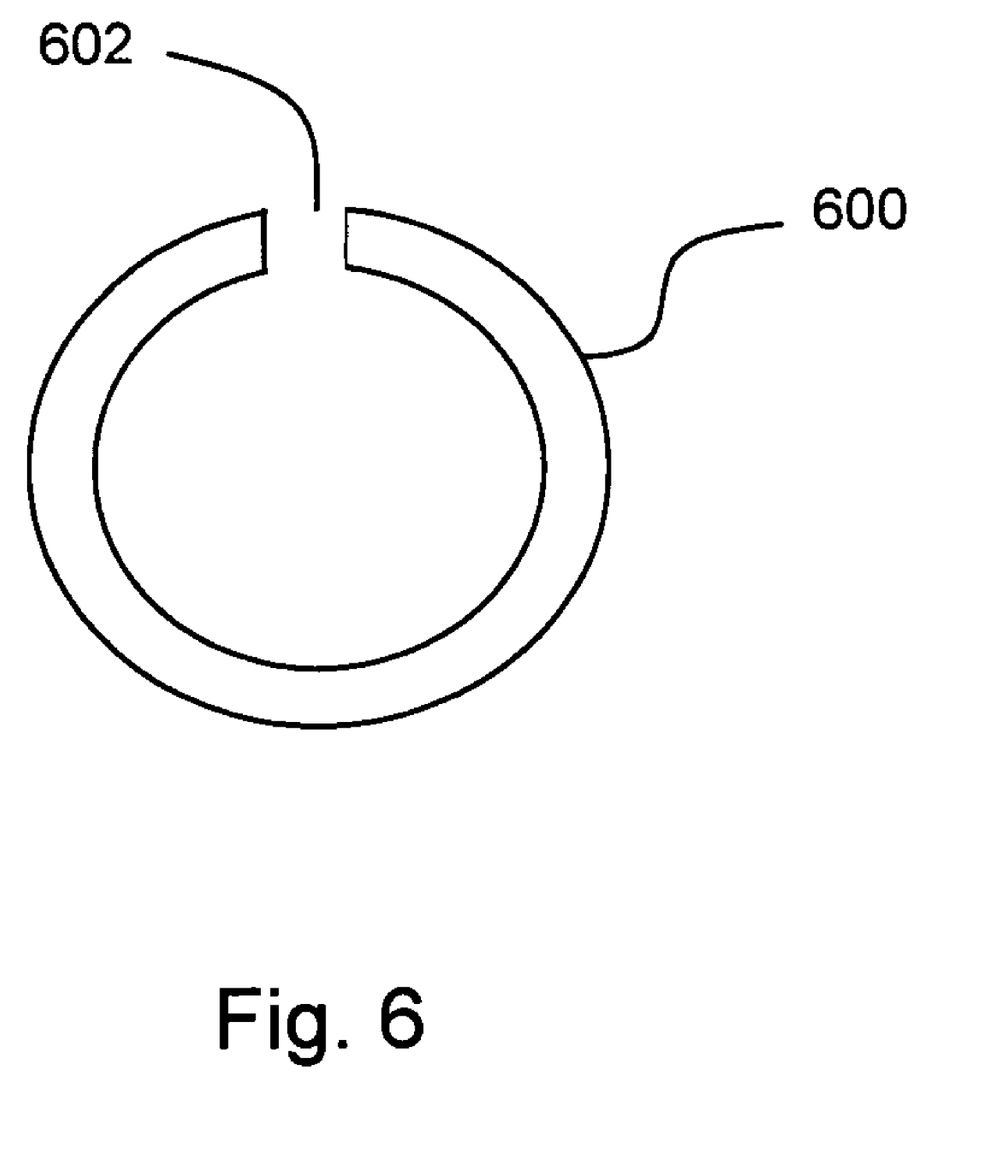
FIG. 6 is a schematic view of a dust-prevention guard for use with the cartridge of the device of FIGS. 1 and 2.

Reference is now made to FIG. 6, which is a schematic view of a dust-prevention guard for use with the cartridge of the device of FIGS. 1 and 2. A dust-prevention guard 600 is shown, being preferably ring-shaped and having a gap 602. Dust-prevention guard 600 is preferably fixedly attached to shaft assembly 116 (FIG. 1A) and covers all of the openings that are on the fluid entry side of the cartridge 102, except for the opening on the fluid entry side that leads to the needle that is located in needle deployment position 202 (FIG. 2A). Dust-prevention guard 600 preferably protects needles 114 from exposure to airborne particles. A thin covering (not shown), preferably formed from paper, may also be employed to cover the injection side of cartridge 102, allowing needles 114 to pierce the thin covering when exiting chamber 200, while protecting needles 114 from dust prior to use. The thin covering may also display printed instructions for using the device.

Figure 7:
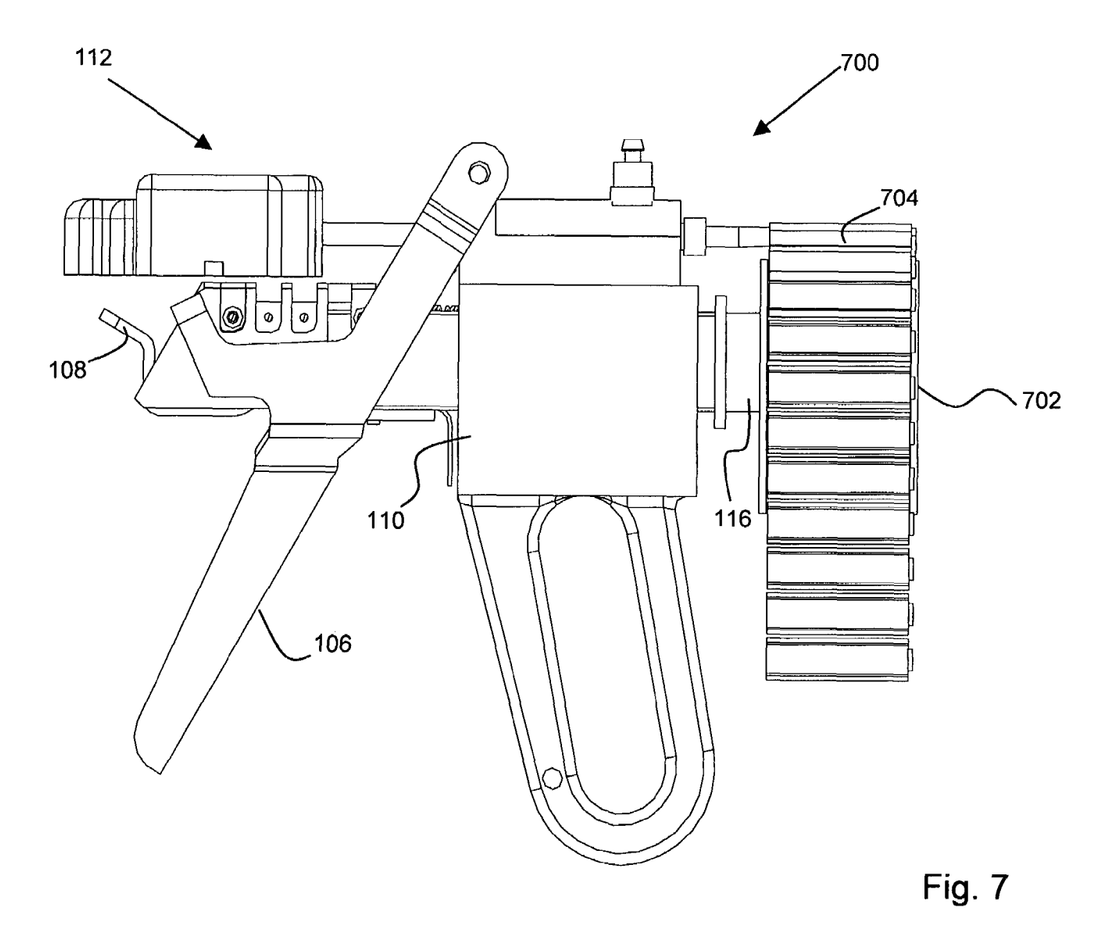
FIG. 7 is simplified side view of a fluid transfer device with needle cartridge ribbon, constructed and operative in accordance with a preferred embodiment of the present invention.

Reference is now made to FIG. 7, which is simplified side view of a fluid transfer device with a needle cartridge ribbon, constructed and operative in accordance with a preferred embodiment of the present invention. A fluid transfer device 700 is shown which operates in a substantially similar manner to fluid transfer device 100 described hereinabove, with the notable exception that a cartridge ribbon 702 is used, in which multiple needle chambers 704 are disposed. Rather than rotate a cylindrical cartridges fluid transfer device 700 advances each needle chamber 704 in cartridge ribbon 702 to needle deployment position 202 using any known mechanism. Cartridge ribbon 702 may be made of any flexible material, such as plastic or fabric.

Figure 8:
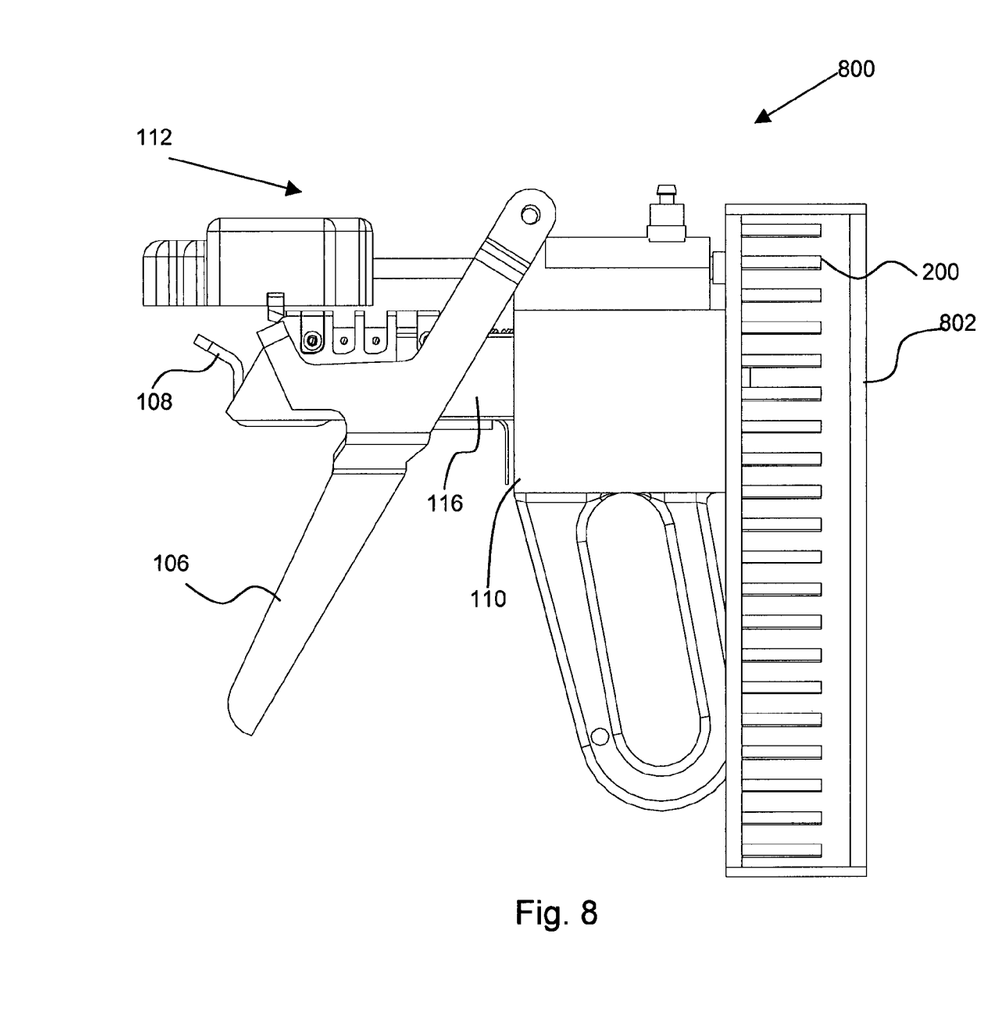
FIG. 8 is simplified side view of a fluid transfer device having a sliding cartridge, constructed and operative in accordance with a preferred embodiment of the present invention.

Reference is now made to FIG. 8, which is simplified side view of a fluid transfer device having a sliding cartridge, constructed and operative in accordance with a preferred embodiment of the present invention. A fluid transfer device 800 is shown which operates in a substantially similar manner to fluid transfer device 100 described hereinabove, with the notable exception that a sliding cartridge 802 is used that is adapted for sliding along any axis that is perpendicular to the axis of shaft assembly 116.

Figure 9:
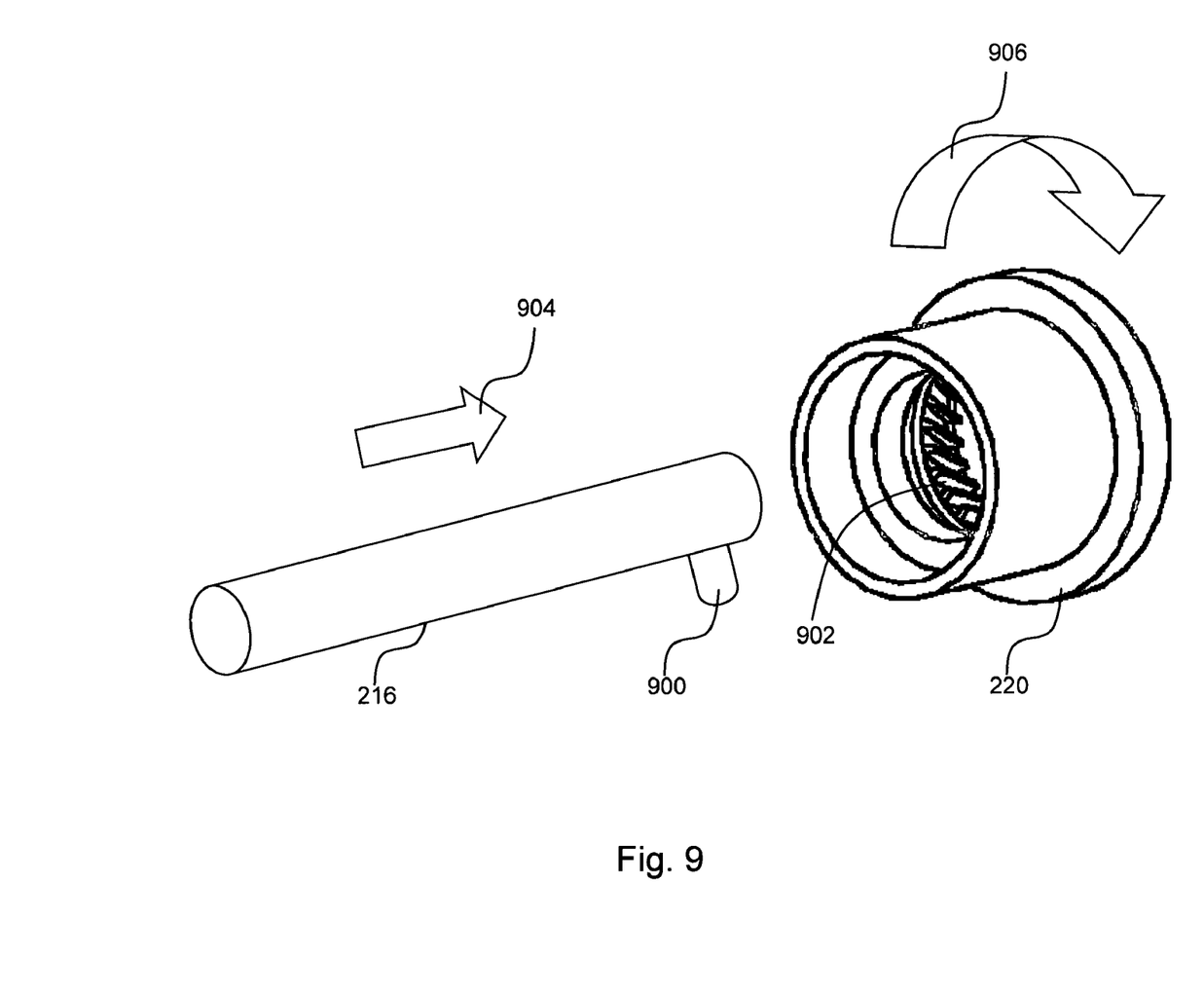
FIG. 9 is a simplified illustration of a rotation mechanism for use with the cartridge of the device of FIGS. 1 and 2.

Reference is now made to FIG. 9, which is a simplified illustration of a rotation mechanism for use with the cartridge of the device of FIGS. 1 and 2. In FIG. 9, inner shaft 216 (FIG. 2A) is shown having a pin 900 preferably extending downward from the end of shaft 216 closest to advancer 220 upon which cartridge 102 may be mounted (not shown). Advancer 220 preferably has a series of gear teeth 902 preferably disposed on its inner circumference at an angle with respect to the longitudinal axis of shaft 216. When shaft 216 moves forward in the direction of arrow 204, pin 900 engages gear tooth 902 (FIG. 2A) which, being set at an angle, causes advancer 220 to rotate in the direction of arrow 906.

It is appreciated that one or more of the elements of the invention described herein may be omitted or carried out in a different order than that shown, without departing from the true spirit and scope of the invention.

While the present invention has been described with reference to one or more specific embodiments, the description is intended to be illustrative of the invention as a whole and is not to be construed as limiting the invention to the embodiments shown. It is appreciated that various modifications may occur to those skilled in the art that, while not specifically shown herein, are nevertheless within the true spirit and scope of the invention.

What is claimed is:

1. A fluid transfer device comprising:
    a cartridge comprising a plurality of needles;
    an advancer operative to selectably advance any of said plurality of needles in said cartridge to a needle deployment position;
    a fluid reservoir shareable by a plurality of said needles; and
    a syringe operative, for each of said needles in said cartridge that is selectably advanced to said needle deployment position, to enter said cartridge, couple with said needle in said needle deployment position, and convey fluid from said fluid reservoir and into said needle via said cartridge,
    wherein said cartridge includes a plurality of needle chambers, each chamber housing one of said plurality of needles, and
    wherein any of said chambers includes at least one needle guard operative to at least partially obstruct an opening of said chamber subsequent to said needle being firstly extended at least partially out of said chamber.

2. A fluid transfer device according to claim 1 and further comprising apparatus operative to at least partially extend said needle out of said cartridge.

3. A fluid transfer device according to claim 2 wherein said apparatus is retractable to urge said needle at least partially back into said cartridge.

4. A fluid transfer device according to claim 1 wherein any of said chambers includes a spring operative to expand when said needle is extended at least partially out of said chamber and contract to retract said needle at least partially back into said chamber.

5. A fluid transfer device according to claim 1 wherein said needle guard is flexed and held in place between said needle and an inner wall of said chamber prior to said needle being firstly extended at least partially out of said chamber, and wherein said needle guard resiliently flattens at least partially across said opening of said chamber subsequent to said extending of said needle.

6. A fluid transfer device according to claim 1 wherein said cartridge is cylindrical and is operative to be rotated to advance any of said needles to said needle deployment position.

7. A fluid transfer device according to claim 1 wherein said cartridge is a ribbon in which a plurality of needle chambers are disposed.

8. A fluid transfer device according to claim 1 wherein said cartridge is a sliding cartridge and is operative to be slid along an axis to advance any of said needles to said needle deployment position.

9. A fluid transfer device according to claim 1 wherein said cartridge is operative to retain said plurality of needles within said cartridge subsequent to fluid conveyance through said plurality of needles.

10. A method for fluid transfer, the method comprising:
    housing each of a plurality of needles in a corresponding one of a plurality of needle chambers disposed in a cartridge;
    selectably advancing a first one of said plurality of needles in said cartridge to a needle deployment position;
    coupling a syringe with said needle;
    conveying fluid from a fluid reservoir through said syringe and said first needle in said needle deployment position via said cartridge;
    selectably advancing a second one of said plurality of needles in said cartridge to said needle deployment position;
    coupling said syringe with said second needle; and
    conveying fluid from said fluid reservoir through said syringe and said second needle in said needle deployment position via said cartridge; and
    at least partially obstructing an opening of any of said chambers subsequent to any of said needles being firstly extended at least partially out of said chamber.

11. A method according to claim 10 and further comprising at least partially extending any of said needles out of said cartridge.

12. A method according to claim 11 and further comprising at least partially retracting any of said needles back into said cartridge.

13. A method according to claim 10 and further comprising causing a spring disposed in any of said chambers to expand when any of said needles is extended at least partially out of said chamber and contract to retract said needle at least partially back into said chamber.

14. A method according to claim 10 and further comprising:
flexing and holding a needle guard in place between any of said needles and an inner wall of said chamber prior to said needle being firstly extended at least partially out of said chamber; and
flattening said needle guard at least partially across said opening of said chamber subsequent to said extending of said needle.

15. A method according to claim 10 and further comprising rotating said cartridge to advance any of said needles to said needle deployment position, where said cartridge is cylindrical.

16. A method according to claim 10 and further comprising sliding said cartridge along an axis to advance any of said needles to said needle deployment position, where said cartridge is a sliding cartridge.

17. A method according to claim 10 and further comprising retaining said plurality of needles within said cartridge subsequent to conveying fluid through said plurality of needles.

* * * * *